United States Patent [19]

Zurinski et al.

[11] Patent Number: 4,542,747
[45] Date of Patent: Sep. 24, 1985

[54] ULTRASONIC APPLICATOR FOR BIOPSY

[75] Inventors: Viktor Zurinski; Ivan Lucic, both of Erlangen; Karlheinz Barthelmes, Baiersdorf, all of Fed. Rep. of Germany

[73] Assignee: Siemens Aktiengesellschaft, Berlin and Munich, Fed. Rep. of Germany

[21] Appl. No.: 556,500

[22] Filed: Nov. 30, 1983

[30] Foreign Application Priority Data

Dec. 2, 1982 [DE] Fed. Rep. of Germany ....... 3244667

[51] Int. Cl.⁴ ............................................. A61B 10/00
[52] U.S. Cl. .................................................... 128/660
[58] Field of Search .............................. 128/660, 24 A

[56] References Cited

U.S. PATENT DOCUMENTS

| 4,029,084 | 6/1977 | Soldner | 128/2 V |
| 4,030,343 | 6/1977 | Lund et al. | 73/67.8 S |
| 4,346,717 | 8/1982 | Haerten | 128/660 |
| 4,363,326 | 12/1982 | Kopel | 128/24 A X |
| 4,387,721 | 6/1983 | Enjoji | 128/660 |

FOREIGN PATENT DOCUMENTS

0039045 4/1981 European Pat. Off. .
2907504 9/1980 Fed. Rep. of Germany .
2906474 11/1980 Fed. Rep. of Germany .

Primary Examiner—Kyle L. Howell
Assistant Examiner—Francis J. Jaworski
Attorney, Agent, or Firm—Thomas H. Jackson

[57] ABSTRACT

An ultrasonic applicator for biopsy which includes a carrying body formed from two extended partial bodies (4, 6). Each partial body has a guide groove (8, 10) introduced in one side. On the surface (12, 14) of each partial body (4, 6), a group (16, 20) of ultrasonic transducer elements is arranged. The two partial bodies can be positioned with respect to one another in such a manner that in a closed position the guide grooves (8, 10) form the guide channel (38) that serves to receive a biopsy needle (37). This lengthwise division of the applicator is advantageous because the row of transducer elements (16, 20) has no gap in the area of the guide channel (38) and when the applicator has both partial bodies in the open position it can be removed, leaving the biopsy needle in place. The partial bodies (4, 6) can be connected with one another in such a way that they can either swivel or be easily removed from one another.

20 Claims, 22 Drawing Figures

ULTRASONIC APPLICATOR FOR BIOPSY

BACKGROUND OF THE INVENTION

The invention concerns an ultrasonic applicator for the ultrasonic examination of an object, which has an extended carrying body with an applicator surface to be directed to the object. Near this application surface are a number of ultrasonic transducer elements which are arranged parallel to one another along the longitudinal axis of the carrying body. There is also a guide channel in the carrying body which extends in the direction of the application surface and is intended to receive a biopsy needle.

The removal of tissue or body fluids from organs or vessels within the body, for example, from the liver or kidneys, for diagnostic purposes by means of suitable devices, such as needles, puncture needles or biopsy needles, is a known procedure. During pregnancy, for example, amniotic fluid can be taken from the uterus for this purpose. Additionally, it is also possible to inject such substances as blood or medication into the fetal body.

In all cases it is extremely important to know the exact position of the biopsy needle in relation to the organ or vessel to be tapped, to prevent unnecessary injuries to areas, such as the placenta when tapping the uterus, or to prevent the erroneous remove of tissue from other parts of the body. In the case of injections it is correspondingly important to avoid injections that miss the target. An ultrasonic applicator used with an ultrasonic echo split-image device provides a known means of continuously checking the tap with the aid of ultrasonics. In particular, this can be accomplished with a rapid ultrasonic split-image display according to the real-time B-scan process. Such an ultrasonic applicator might consist of a carrier element which has a substantial number of ultrasonic transducer elements arranged in a row parallel to one another on the application surface. By the rapid successive activation of the individual ultrasonic transducer elements during the scanning sequence, the part of the body to be tapped is scanned line-by-line at a given section level by the generated ultrasonic beam. When an image of the ultrasonic echo pulses is formed on the screen of the display of the split-image device, a preferred split image level is selected for the direction of the tap. The biopsy needle is also clearly visible on the screen when introduced at this level, because the needle material, usually a metal, produces an easily distinguishable ultrasonic contrast with the surrounding biological tissue. Despite good visual monitoring in the scanning area aiming problems have persisted. Thus, although the movement of the needle in the tissue could indeed be followed directly with the eye on the screen of the display, this did not take place until the needle had actually arrived within the range of the ultrasonic scanning waves at the scanning section level. Until the desired range was reached the insertion process was conducted blindly.

U.S. Pat. No. 4,029,084 discloses how to avoid undesirable injuries to the tissues, due to frequent corrections of the tap, and due to delays in the tapping procedure. It states that instead of a round channel precisely adapted to the needle, the carrying body should be provided with a guide slot extending along it lengthwise for the puncture needle. The guide slot should narrow from a prescribed maximum length, which is measured off on the face opposite to the application surface of the carrying body, to a minimum slot length at the application surface itself. As a result the slot is V-shaped and located in the central part of the carrying body. Therefore, a guide channel that is closed on all sides is involved. This has the disadvantage that the ultrasonic array cannot be separated immediately from the implanted biopsy needle and removed from the patient.

It is desirable to use the same ultrasonic applicator in quick succession for various patients and biopsies, one after the other. For this purpose it is necessary for the applicator to be capable of being quickly and simply cleaned and then sterilized. One way of meeting these requirements would be to slip a sterile plastic bag over the actual ultrasonic application for each use. Then, after completion of the biopsy and before any subsequent use, this bag can be exchanged for another one. The conventional ultrasonic applicator with a central guide channel would hardly be suitable for such an operation, since the bag would be perforated when the biopsy needle was inserted. A further disadvantage is the fact that the row of ultrasonic transducer elements has a gap of a single transducer element or several transducer elements at the point on the application surface where the guide slot opens. Since individual transducer elements are missing at this point, the scanning sequence of the ultrasonic array is interrupted, and the resulting image quality precisely at the point of insertion is reduced.

An ultrasonic applicator in which the guide channel is located in the side wall rather than in the center of the extended carrying body is also commercially available. This guide channel, which accordingly opens to the side, is also frequently V-shaped. With this model, the ultrasonic applicator can be removed from the patient while the biopsy needle remains implanted. However, in this case it is also impossible to put a new sterile bag over the applicator after every patient in order to step up the number of biopsies. Actual use of the applicator has shown that in the area of the guide channel, particularly at its narrow end near the application surface, there is a folding of the material that cannot be controlled. Therefore, a risk of causing damage to the bag when the biopsy needle is put in place exists. The scanning sequence in this known applicator is also interrupted, because individual ultrasonic transducer elements are missing in the middle section, at the outlet of the guide channel.

German patent specification No. 29 06 474 discloses a method for introducing a needle guide block or guide slot element into an opening introduced in the carrying body of an applicator. The applicator contains the actual guide channel and is intended to hold the biopsy needle. Additionally, the needle guide block can be removed from the carrying body. This allows the guide channel, which comes into direct contact with the needle, to be immediately sterilized. Accordingly, hygiene and sterilization problems are largely avoided. Thus only the guide slot element, rather than the entire carrying body of the ultrasonic transducer probe, has to be sterilized prior to its use. A gas sterilization process or the like can be used and then the sterilized element can be set into the carrying body. However, even with this applicator the disadvantages mentioned above with regard to performing an increased number of biopsies and the use of a sterile bag are encountered. Furthermore, this design also has the previously described disadvantage that individual ultrasonic transducer elements are missing at the point at which the opening for the insertion of the needle guide block opens into the application surface.

In published German patent application No. 29 07 504 an ultrasonic applicator is described in which a guide device is mounted in the middle between two ultrasonic sending and receiving systems. Here, too, a number of transducer elements are missing between the two systems. These two systems are alternately operated so that a partial overlapping takes places on the screen of the display. This could also be expressed as follows: In order to be able to obtain a better view of the biopsy needle when it is inserted, in spite of the interruption of the scanning sequence that occurs at the outlet of the channel, a special program is provided here for the scanning of the ultrasonic transducer elements. However, such a special program must be provided for in the electronic system and requires relatively expensive electronic equipment. Since altered focusing is used in the area where the biopsy needle has been inserted it is possible that in this area a different tissue sample might appear on the screen, with impaired lateral resolution. In this model it also does not make sense to cover the carrying body with a sterile bag.

SUMMARY OF THE INVENTION

The object of this invention is to provide an ultrasonic applicator which can be separated from the biopsy device after it has been introduced, which is easy to clean and which avoids any interruption of the scanning sequence in the area of the guide channel.

This object is accomplished by constructing the carrying body from two extended partial bodies, each of which has a guide groove introduced on its side; by dividing the number of ultrasonic transducer elements into two groups; by providing each partial body with a surface area along which one of these groups of ultrasonic transducer elements is arranged; and by making it possible to position the two partial bodies with respect to one another in such a manner that in a closed position the guide grooves from the guide channel that serves to guide the biopsy needle, and the two surface areas from the application surface.

Accordingly, the two extended partial bodies in the closed position, in which the ultrasonic radiation and image formation take place, can be regarded as a single ultrasonic array, which is divided lengthwise. The basic principle of the invention can therefore also be summarized as follows: the ultrasonic applicator consists of two partial applicators connected to one another, which in a closed position together form the guide channel and are operated parallel to one another.

It has already been stated that the two partial bodies can be positioned with respect to one another. This can be accomplished either by making the two partial bodies separable or removable from one another, or else by swivelly connecting them together.

The two partial bodies or halves in this case can be swivelly connected with one another, for example, by a pivot. In particular, it can be arranged so that the two partial bodies swivel about an axis that is essentially perpendicular to the longitudinal axis of the two partial bodies. If at least one of the two partial bodies is swiveled out of the closed position or removed from the other partial body, the biopsy needle is released, and the ultrasonic applicator can be removed from the patient, leaving the needle behind. Since at this point the two guide grooves are also free, disinfecting can take place quickly and effectively. There is no interruption or gap in the row of ultrasonic elements in the area where the guide channel opens into the application surface.

It must be emphasized in particular that either a sterile cover or a sterile bag can be slipped over each of the two partial bodies, and can be changed after the applicator has been used. These two covers or bags can in this case, like the two fingers of a surgical glove, as fastened to a larger covering, which includes the pivot and the feeder cable for the individual ultrasonic transducer elements. Alternatively, they may be an integral part of this covering.

Other features and advantages of the invention will be apparent from the following description of the preferred embodiments, and from the claims.

For a full understanding of the present invention, reference should now be made to the following detailed description of the invention and to the accompanying drawings.

BRIEF DESCRIPTION OF THE DRAWINGS

Embodiments of the invention are explained with reference to the figures described below. In the figures the same reference numbers are used for the same or similar components.

DETAILED DESCRIPTION

Figure 1:
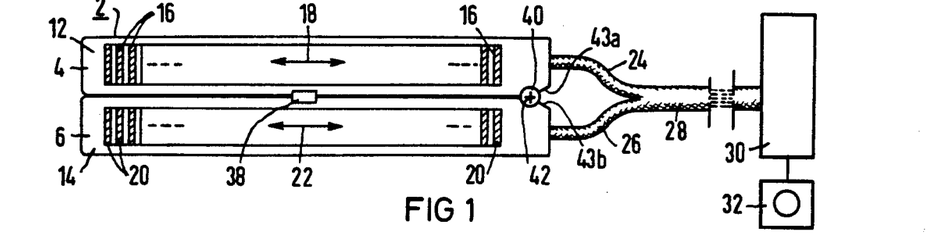
FIG. 1 shows a top view looking at the application surface of a two-part ultrasonic applicator according to the invention, which is in the closed position.
Figure 2:
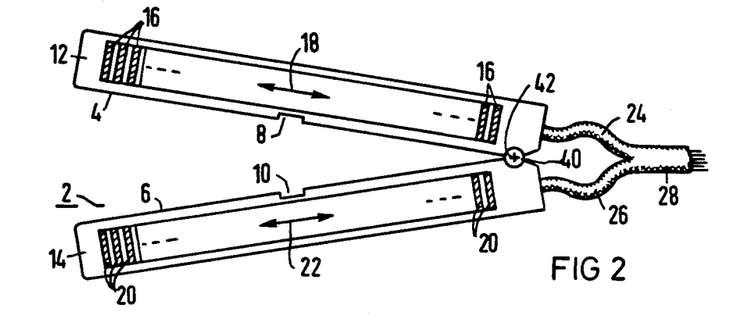
FIG. 2 shows the two-part ultrasonic applicator of FIG. 1 in an open swivel position.
Figure 3:
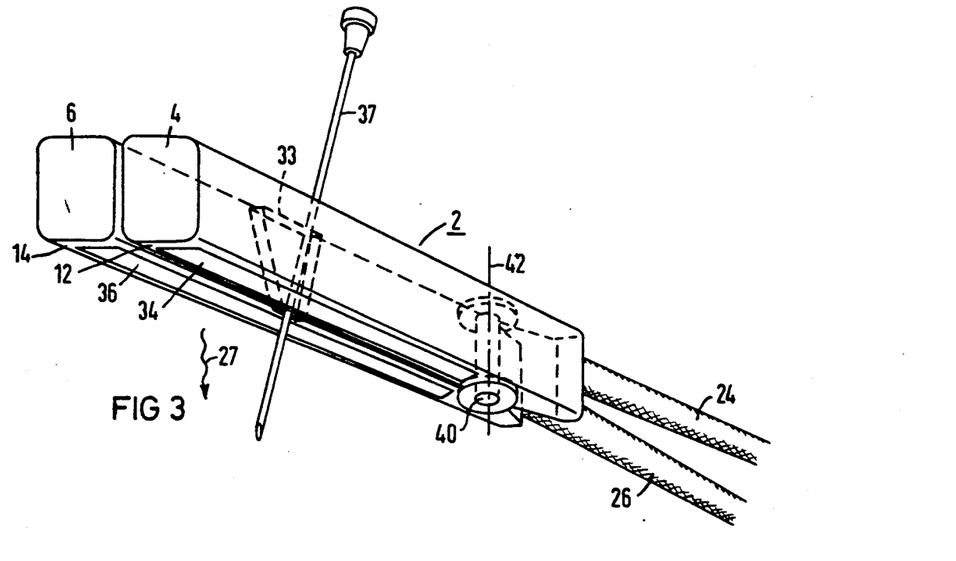
FIG. 3 shows a perspective view of the ultrasonic applicator of FIGS. 1 and 2, looking at the application surface.

In FIGS. 1 to 3 the basic construction of ultrasonic applicator 2 according to the invention is shown. FIGS. 1 and 2 show a view of the application surface, and FIG. 3 shows the ultrasonic applicator in perspective. Ultrasonic applicator 2 operates in conjunction with an ultrasonic echo split-image device. In particular, it operates according to the real-time B scan process.

As shown in FIG. 1, the extended carrying body of the applicator consist of two array-halves or partial bodies 4 and 6, which are likewise extended. The two carrying bodies 4 and 6 are in the form of parallelepipeds and are preferably made of a hardened plastic, which can be provided with additives of heavy metals. Each of the two partial bodies 4 and 6 has a guide groove, numbered respectively 8 and 10, introduced in its side and opening outward. These guide grooves 8 and 10 run through the partial body from surfaces 12 and 14, shown in the figures, to the opposite upper side which is parallel to them.

First partial body 4 has on surface 12 or in its vicinity, a first group of ultrasonic transducer elements 16 which are arranged parallel to one another along length 18 of partial body 4. Correspondingly, second partial body 6 has on its surface 14 or in its vicinity, a second group of similar ultrasonic transducer elements 20 which are arranged parallel to one another along length 22 of partial body 6. First ultrasonic transducer elements 16 are connected to first connecting cable 24 and second ultrasonic transducer elements 20 to second connecting cable 26. All transducer elements 16 and 20 have the same length and the same width. Their distance from one another is also the same. In the closed position the two groups are virtually parallel to one another. A deviation from this arrangement is explained later on with the aid of FIG. 21. The direction of the radiation from elements 16 and 20 is designated by 27.

It is particularly noteworthy that in both the first and the second group none of transducer elements 16 and 20 are missing in the area of needle guide grooves 8 and 10. As a result, during the scanning process in the area of guide grooves 8 and 10 there is no discontinuity, and accordingly no diminution in the quality of the ultrasonic image. A homogeneous presentation of the tissue is achieved laterally, or parallel to the array. This presupposes that neighboring ultrasonic transducer elements 16 and 20, which are viewed along lengths 18 and 22, are arranged at the same length and are accordingly positioned for practical purposes in a row when the applicator is closed and are electrically connected in parallel. This can be seen from the fact that connecting cables 24 and 26 pass into common power cable 28. This cable is in turn connected with control device 30, which represents the familiar sending and receiving elements of the ultrasonic echo split-image device and is also responsible for evaluating the echo signals that are received. The presentation then takes place in a familiar manner of recording or display device 32. Control device 30 and display device 32 are conventional equipment, and therefore they are only shown in block form.

An examination of FIGS. 1 to 3 reveals that partial bodies 4 and 6 are mirror images of each other with regard to their form and with regard to transducer elements 16 and 20 which are mounted on them.

Surfaces 12 and 14 can be provided with connecting layers 34 and 36 between the surfaces and transducer elements 16 and 20.

Partial bodies 4 and 6 are swivelly connected with one another in the manner of a clothes pin; specifically, in such a way that in the closed position shown in FIG. 1, two guide grooves 8 and 10 form guide channel 38 that serves to guide biopsy needle 37 (see FIG. 3) or another biopsy device. This guide channel 38 thus extends from the upper surface of carrying body 2 to the application surface. The application surface in this case is formed by surfaces 12 and 14. In order to permit the abovementioned swiveling, pivot 40 has been provided. In this embodiment, as shown in FIGS. 1 to 3, pivot 40 is introduced in the outer end of two partial bodies 4 and 6 that is nearest to the cable in the sides that face one another. It is preferable to design pivot 40 in such a manner that the two partial bodies can be easily separated from one another.

Swivel axis 42 which is formed by pivot 40, will preferably be perpendicular to longitudinal axes 18 and 22 of partial bodies 4 and 6. An embodiment of pivot 40 that connected two rectangular partial bodies with one another at the sides that face one another is explained below with the aid of FIGS. 11 and 12.

It should be emphasized once again that pivot 40 is placed virtually at the outside end of partial bodies 4 and 6 that is nearest the cable. The edges projecting beyond it are beveled at the outer points of side surfaces 43a, 43b, so as not to impede the opening process. In FIG. 1 partial bodies 4 and 6 are shown in the closed position. In this closed position, biopsy device 37 (shown in FIG. 3) in inserted through guide channel 38 into the object to be investigated (i.e. the patient) with ultrasonic image monitoring. After insertion has been completed, partial bodies 4 and 6 can be brought into the open position shown in FIG. 2 by swiveling them around swivel axis 42. Now ultrasonic applicator 2 can be taken off the object to be investigated and removed. In the process, biopsy needle 37 can remain, just as before, in the tissue of the patient which is under investigation. Ultrasonic applicator 2 can then be cleaned and disinfected in the open position. In order to facilitate this procedure, partial bodies 4 and 6 can be separated from one another at pivot 40.

Accordingly, ultrasonic applicator 2 consists of two partial bodies 4, 6 and 16, 20, that are swivelly connected with one another, can be separated from one another, can form guide channel 38 with one another in the closed position and at the same time are operated in parallel with one another.

Figure 4:
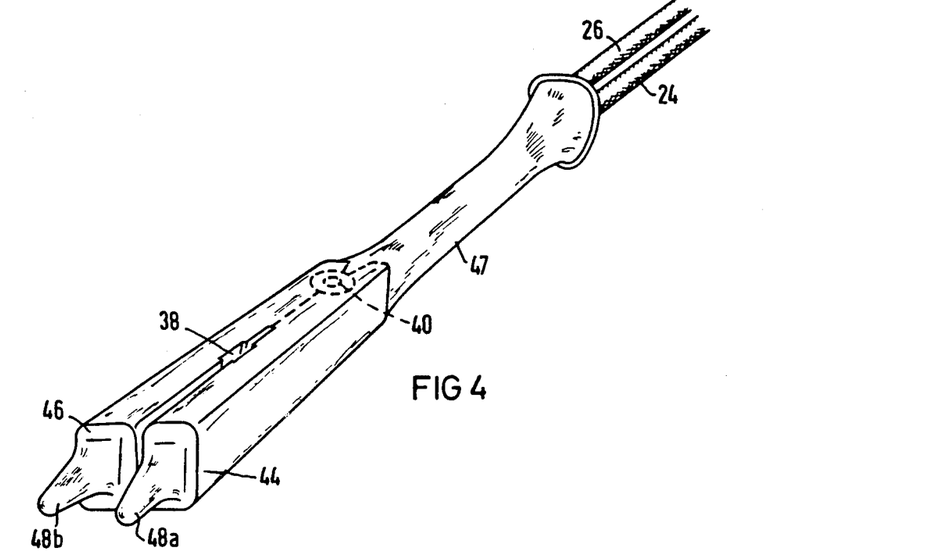
FIG. 4 shows a perspective top view of a two-part ultrasonic applicator, which is enclosed in a two-fingered bag.

It should be emphasized in particular that in the ultrasonic applicator shown in FIGS. 1 to 3, nothing further has to be done to permit a finger-shaped cover or a bag, 44 and 46, to be slipped over each of the partial bodies 4 and 6. This is illustrated in FIG. 4. The finger-shaped covers 44, 46 are made of a stretchable plastic and sterilized before use. Like the fingers of a surgical glove, they open into common covering 47, which covers pivot 40, the connecting cable 24, 26 and, if necessary, power cable 28. After applicator 2 has been used, covers 44 and 46 and common covering 47 can be immediately removed and exchanged for another cover for a fresh application. It should be noted that covers 44, 46, which can be made, for example, of latex or some other rubber-like material, are not damaged when biopsy needle 37 is introduced into guide channel 38, since they leave the actual channel free and do not create folds there.

According to FIG. 4, finger-shaped bags 44, 46 can be provided at the unconnected ends of partial bodies 12 and 14 with reservoirs 48a and 48b for a connecting medium, which can be filled into the covering 44, 46, 47.

Figure 5:
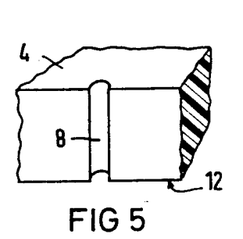
FIGS. 5 to 7 show various designs for the shape of the guide grooves in the partial bodies.

In an emergency partial bodies 4 and 6 can actually be inserted into two adjacent fingers of a surgical glove made of latex. In FIG. 5, it is shown that guide groove 8 can have a semicircular cross-section. Opposite guide groove 10 (not shown here) is designed in the same way. When partial bodies 4 and 6 are put together a round cross-section for guide channel 38 is formed in the closed position. The two guide grooves in this case only have to be a little deeper than the half-diameter of needle 37, which will then be seated relatively snugly in guide channel 38.

Figure 6:
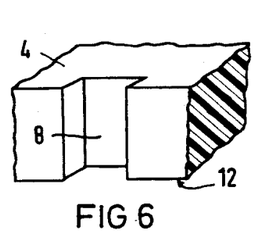

However, according to FIG. 6, a rectangular shape may also be selected for guide groove 8. As can be seen, the two sides of guide groove 8 that are opposite to one another, have been made parallel to one another. In the closed position of partial bodies 4 and 6, there is thus formed guide channel 38 with a rectangular cross-section, whose dimensions remain the same from the surface of the applicator to the application surface.

Figure 7:
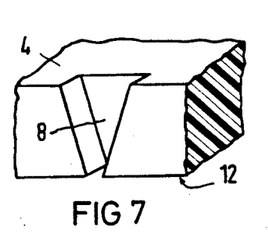

On the other hand, according to FIG. 7, guide groove 8 can also have the form of a rectangular trapezoid. This guide groove thus has a V-shape, with its point in the direction of application surface 12.

Thus, in the closed position of partial bodies 4 and 6 wedgeshaped guide channel 38 is obtained.

Naturally, other groove shapes than those shown in FIGS. 5 to 7 can be used.

Since, as shown in FIGS. 1 to 3, ultrasonic transducer elements 16, 20 are arranged in two rows in the vicinity of guide channel 38 as well, there is no interruption of the ultrasonic image at application surface 12. It should likewise be pointed out that for all the groove shapes shown in FIGS. 5 to 7, a sterile bag 44 can be used which is slipped over respective partial body 4.

Figure 8:
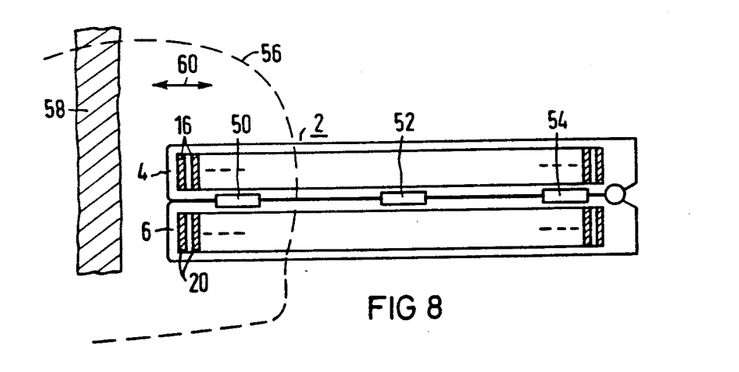
FIG. 8 shows a top view looking at the application surface of an ultrasonic applicator according to the invention with several guide channels.

In FIG. 8 there is shown an embodiment of an ultrasonic applicator in which partial bodies 4 and 6 each have several guide grooves and accordingly form several guide channels 50, 52 and 54. In this embodiment guide channel 52 can be centrally located, while guide channels 50 and 54 are located outside the center half of partial bodies 4 and 6.

The location of guide channels 50 and 54 at the left or right side of ultrasonic applicator 2 can under certain circumstances be of extraordinary advantage. An example of their application is indicated in FIG. 8. It is assumed that an organ or vessel 56 is to be tapped with biopsy needle 37 and that this organ 56 lies in the immediate vicinity of rib 58 of the human body. It is further assumed that this organ or vessel 56 is subject to a certain movement, due, for example, to pulsating blood or the breathing of the patient. The line of movement of organ 56 is designated by 60. In this case, ultrasonic applicator 2 can be placed on the patient near rib 58 and it can nevertheless be insured that the organ can be reached with needle 37 through guide channel 50, which is located at the outermost end. In the process, organ 56 cannot move out of the scanning level, and accordingly out of the ultrasonic image, as the result of body respiration. A biopsy using central guide channel 52 would obviously not be successful. The pivot 40 does not interfere. Here, too, the advantage mentioned above is again apparent; namely that even in the immediate vicinity of guide channel 54 all the transducer elements 16 and 20 that are needed for an uninterrupted scanning operation are available. Since there are no gaps in the groups of transducer element 16 and 20, in this case, a perfect image in the area of the insertion is again created.

Figure 9:
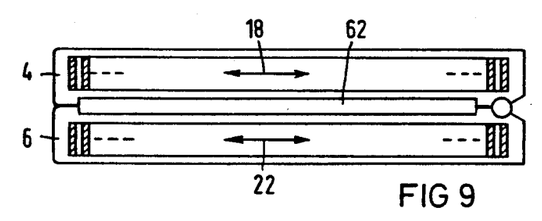
FIG. 9 shows a top view looking at the application surface of an ultrasonic applicator according to the invention with a single extended guide channel.

While according to FIG. 8, guide channels 50, 52, 54, which have relatively narrow lateral limits, can be located at desired points along the division of two-part ultrasonic applicator 2, according to FIG. 9 single guide channel 62 that extends for an extremely long distance on longitudinal axes 18, 22 has been provided. With this channel 62 the application point and the insertion point for biopsy needle 37 can be selected more or less arbitrarily. Extended guide channel 62 can in this case run over virtually the entire length of partial bodies 4 and 6 without producing a gap in the row arrangement of individual ultrasonic transducer elements 16 and 20.

Figure 10:
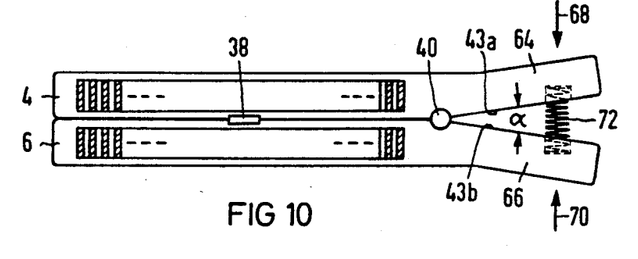
FIG. 10 shows a two-part ultrasonic applicator according to the invention with operational controls used to open it easily.

FIG. 10 shows a modification of the ultrasonic applicator illustrated in FIGS. 1 to 3. This applicator is distinguished by the fact that ends 64 and 66 of partial bodies 4 and 6 respectively, that are located to the right of pivot 40, are elongated, and, in addition, bent away from one another. Bent-out end pieces 64 and 66 in this case are used as operating controls or hand grips. If force is exerted in the direction of arrows 68 and 70, partial bodies 4 and 6 are swiveled open, and biopsy needle 37 located in guide channel 38 is released. Between end pieces 64 and 66, it is preferable to place pressure spring 72. This insures that partial bodies 4 and 6 are normally held in the closed position. To open them, as in the case of a clothespin, the force of spring 72 must be overcome. After the applicator has been opened to angle a, the outer inside surfaces 43a, 43b of the end pieces 64 and 66, operate as a stop.

Figure 11:
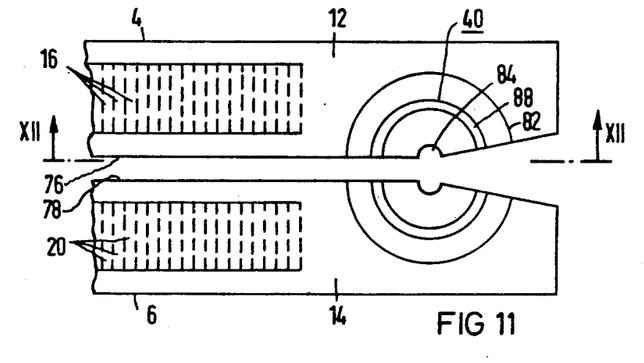
FIG. 11 shows a top view of a pivot that can be used in the embodiments shown in FIGS. 1 to 10.
Figure 12:
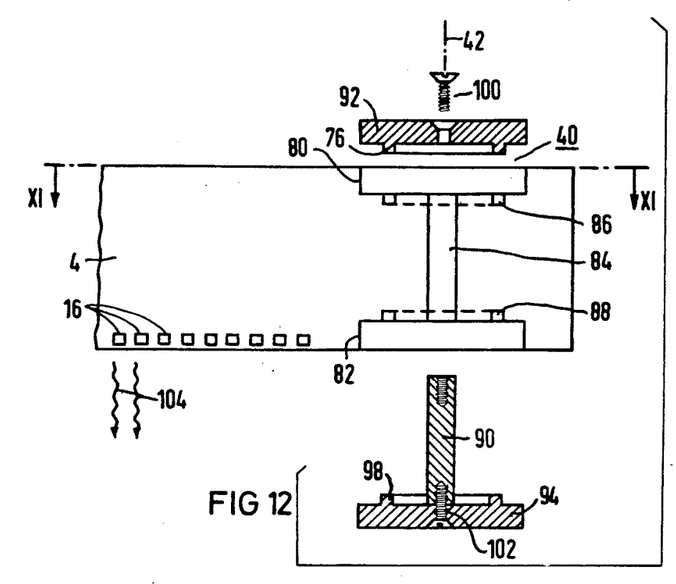
FIG. 12 shows a side view of a partial body with a pivot according to FIG. 11, with the components forming the pivot shown in cross-section.

FIGS. 11 and 12 show an embodiment of pivot 40. Here FIG. 11 shows a cutaway view of the application surface of the ultrasonic applicator, in which, to give a better view, partial bodies 4 and 6 are shown separated from one another and a screw device with retaining plates or guide plates has been removed. FIG. 12 provides a view of partial body 4 along the line XI—XI, in which the screw device to be inserted is shown in cross-section.

The easiest way to understand FIG. 1 is to assume that inner sides 76 and 78 of partial bodies 4 and 6 respectively, are in contact with one another. Then both the upper surface and the application surface 12, 14 each contain a cylindrical recess 80 and 82 respectively. These two cylindrical recesses 80 and 82 are connected by round channel 84, which runs along swivel axis 42. Each cylindrical recess 80 and 82 also has at its bottom, a ring-shaped groove 86 and 88 respectively. As is evident from their function, these grooves 86 and 88 serve to prevent relative motions of partial bodies 4 and 6 in the direction of application surface 12, 14.

In connecting channel 84, rotating axle 90 has been inserted in such a manner that it free to rotate. Rotating axle 90 is fastened to two cylindrical end plates or guide plates 92 and 94, each of which have a projecting ring lug 96 and 98 respectively, and which fit into recesses 80 and 82. Screws 100 and 102 are used to fasten guide plates 92 and 94 to rotating axle 90. The direction of the radiation from the individual ultrasonic transducer elements is designated here by 104.

Figure 13:
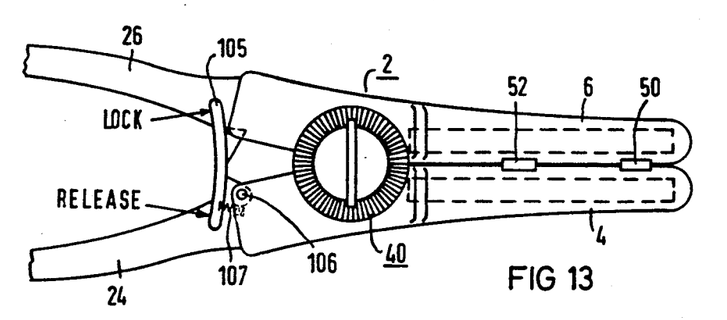
FIG. 13 shows another embodiment of the ultrasonic applicator according to the invention with a locking mechanism in a top view.

Pivot 40 shown in FIGS. 11 and 12, has been designed in such a manner that it can be quickly taken apart, so that the individual pieces can be quickly cleaned and disinfected, and may rapidly be put back together. In FIGS. 13 to 17 another ultrasonic applicator 2 for biopsy applications is shown. For the most part, this applicator 2 corresponds to the one shown in the previous figures. It again involves an ultrasonic array that is divided lengthwise, with two partial bodies 4 and 6 forming two guide channels 50 and 52. This applicator 2 is provided with locking mechanism 105. This locking mechanism includes a lever with a lug 105a which swivels on axis 106. Swivel axis 106 is located at the extreme left end of first partial body 4 and is perpendicular to its longitudinal axis. In the closed position, pressure spring 107 holds lug 105a pressed against the extreme left end of second partial body 6. FIG. 13 thus shows the locked position. If the lock is to be released, pressure is exerted against the force of spring 107 on locking mechanism 105, which then swivels around swivel axis 106, causing lug 105a to be released from the left end of partial body 6. Now, be pressing together the two left ends of partial bodies 4 and 6, applicator 2 can be changed from the closed position into the open position.

Figure 14:
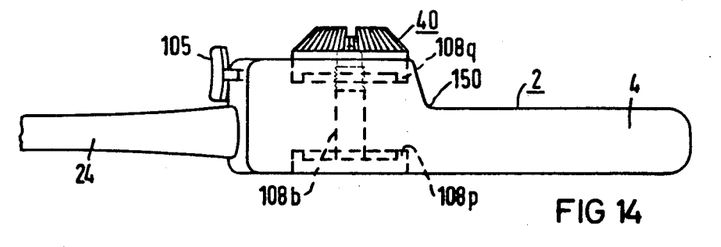
FIG. 14 shows the embodiment according to FIG. 13 in a side view.
Figure 15:
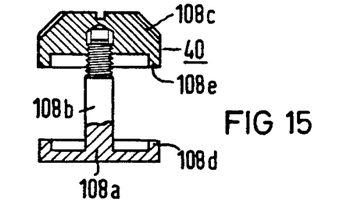
FIG. 15 shows bearing elements for the pivot shown in FIGS. 13 and 14.
Figure 16:
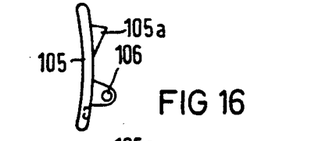
FIGS. 16 and 17 show the locking mechanism according to FIGS. 13 and 14.
Figure 17:
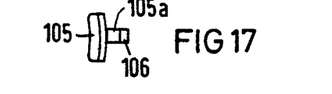

It can be seen from FIGS. 13 to 15 that pivot 40 is constructed in the same manner as shown in FIGS. 11 and 12. In the present case it includes lower plate 108a with threaded bolts 108b, which is introduced from below into an approximately designed cylindrical recess in the application surface of partial bodies 4 and 6. Threaded bolt 108b screws into upper plate 108c, which is introduced into an approximately designed recess on the upper side of partial bodies 4 and 6. Upper plate 108c in this case is designed as a nut. Both plates 108a and 108c have at their edges ring-shaped guides 108d and 108e that fit into correspondingly formed ring-shaped guide grooves 108p and 108q.

Another important feature of the embodiment shown in FIGS. 14 to 17, is that applicator 2 includes two parts of unequal thickness. These two parts overlap with one another in a tapered edge 150. The thinner, right-hand part, in which guide channels 50, 52 are located, is designed in this case for special ease in handling. In the thicker, left-hand part, which also provides a connection for cables 24 and 26, pivot 40 is located.

Figure 18:
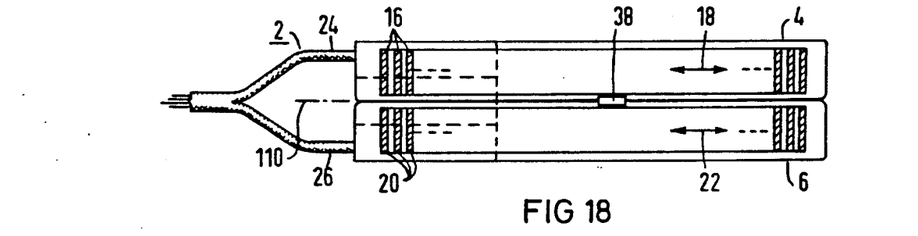
FIG. 18 shows another embodiment of an ultrasonic applicator according to the invention, in which the swivel axis is parallel to the longitudinal axis of the two partial bodies, in a view looking at the application surface.
Figure 19:
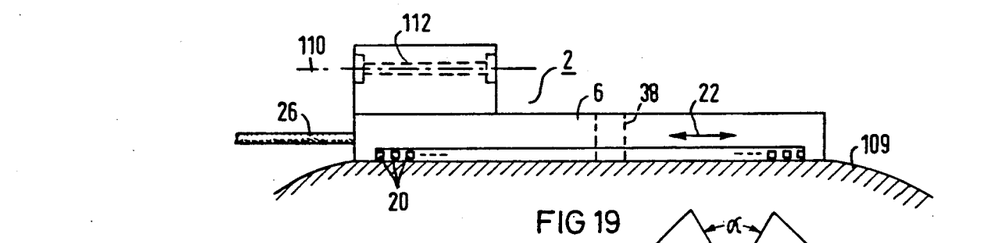
FIG. 19 shows a side view of the embodiment according to FIG. 18.
Figure 20:
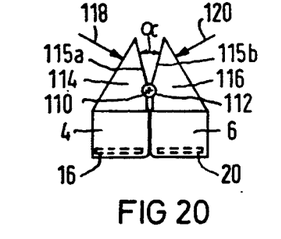
FIG. 20 shows a front view of the embodiment according to FIGS. 18 and 19.

In FIGS. 18 to 20, an embodiment of ultrasonic applicator 2 that is different in principle is shown. In this case it is again provided that two partial bodies 4 and 6, which form a guide channel between them, can be swiveled apart, or rather hinged apart, in which case a biopsy needle that has been inserted in guide groove 38 is released.

In the embodiment shown (FIGS. 18 and 19), applicator 2 is then drawn away to the left. In FIG. 19, applicator 2 is placed on surface 109 of a patient.

In detail this embodiment provides (FIGS. 18 to 20) for swivel or hinge axis 110 to run parallel to longitudinal axes 18 and 20 of partial bodies 4 and 6. In the embodiment shown this hinge axis 110 has been specially placed above the upper surface of partial bodies 4 and 6. It is therefore located outside of and virtually parallel to the upper surface of partial bodies 4 and 6. In principle, hinge axis 110 can be designed in any desired manner, for example in the form of a hinge 112, as shown in FIGS. 11 and 12 or in FIGS. 13 to 15. As can be seen particularly in FIG. 20, projections 114 and 116 are fastened to the upper surfaces of partial bodies 4 and 6 and serve to activate the hinging effect. Above hinge 112, these projections form an angle α with one another, so they do not get in one another's way when the apparatus is rotated outward. The rotation outward is done by hand, with the force being applied in the direction of arrows 118, 120. The faces that form the angle α with one another then act simultaneously as a kind of stop. They determine the maximum angle to which partial bodies 4 and 6 can be rotated outward from one another.

It should also be noted that for a given arrangement of swivel axes 40 and 110, it is desirable to design array pivots 42 and 112 so that partial bodies 4 and 6 are kept parallel to one another during the biopsy by springs or catches. After the catches are released, applicator 2 can then be removed even when biopsy needle 37 is in place.

Figure 21:
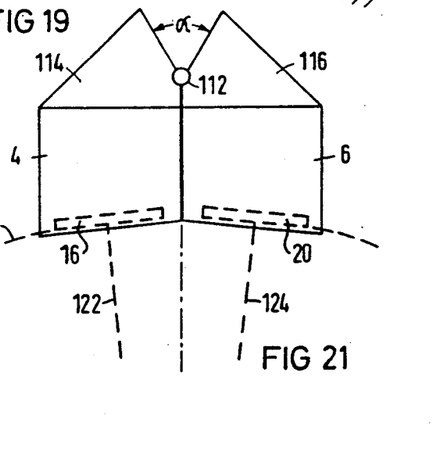
FIG. 21 shows a front view of another embodiment of the applicator according to the invention, in which the transducer elements of the two groups are brought into the focusing position.
Figure 22:
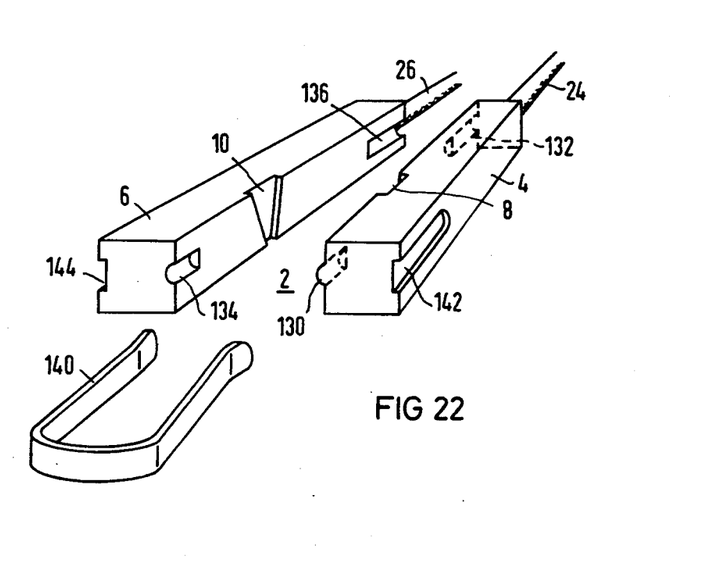
FIG. 22 shows a perspective view of another applicator embodiment, in which the two parts of the applicator are not swivelly connected, but can instead be easily removed from one another.

A focusing of the ultrasonic beam obliquely to the direction of the scan, in other words, obliquely to longitudinal axes 18 and 22 of partial bodies 4 and 6, can be accomplished by means of lenses, through concave grinding on the application surface or through tilting the two groups of ultrasonic transducer elements 16 and 20. This last possibility is indicated in FIG. 21. From FIG. 21 it can be seen that the levels of the two groups of elements 16 and 20 have been displaced by a small angle from one another. The directions 112 and 124 of the radiation converge. Instead of this displacement, it is also possible to choose transducer elements that are bent or curved along arc 126. Elements 16 and 20, which are shown in FIG. 21 as being displaced at an angle, adhere as closely as possible to this arc 126. FIG. 22 shows an embodiment of an ultrasonic applicator in which (unlike the preceding FIGS. 1 to 21) partial bodies 4 and 6 are not swively connected with one another. Instead, in this embodiment partial bodies 4 and 6 can be easily placed side by side and joined together. They can then be separated from one another and removed from one another with equal ease. For this purpose, the inner surface of partial body 4 has two guide springs 130 and 132, extending in a longitudinal direction, which fit into holding grooves 134 and 136 in the opposite lateral faces of partial body 6. To clamp together partial bodies 4 and 6, spring clamp 140 has been provided. Clamp 140 is approximately U-shaped and can be made out of plastic or metal. Clamp 140 is pushed over the outer faces of the two partial bodies 4 and 6, and thereby holds them together in the closed position. To facilitate handling and to stabilize partial bodies 4 and 6 in a position parallel to one another, the outside faces can be provided with lengthwise clamp guides 142 and 144 in the form of grooves, into which the legs of clamp 140 reach in the closed position. Thus, to clean the ultrasonic applicator all that needs to be done is to remove clamp 140. Then partial bodies 4 and 6 can easily be removed from one another.

There has thus been shown and described novel apparatus for an ultrasonic applicator for biopsy which fulfills all the objects and advantages sought. Many changes, modifications, variations and other uses and applications of the subject invention will, however, become apparent to those skilled in the art after considering this specification and the accompanying drawings which disclose embodiments thereof. All such changes, modifications, variations and other uses and applications which do not depart from the spirit and scope of the invention are deemed to be covered by the invention which is limited only by the claims which follow.

What is claimed is:

1. In an ultrasonic applicator for the ultrasonic examination of an object, having an extended carrying body, which has an application surface to be directed to the object and, in the vicinity of this application surface, a number of ultrasonic transducer elements, which are arranged parallel to one another along the longitudinal axis of the carrying body, and with a guide channel in the carrying body which extends toward the application surface and is intended to receive a biopsy needle, the improvement comprising said carrying body being made up of two extended partial bodies each of which has a guide groove on one side, the two extended bodies being connected at a means for permitting the two extended partial bodies to move from a closed to an open position, said ultrasonic transducer elements being divided into two groups, each partial body having a surface along which one of said two groups of ultrasonic transducer elements is arranged, both partial bodies being positioned with respect to one another in such a manner that in the closed position said guide grooves form said guide channel that serves to guide said biopsy needle, and said two partial body surfaces form said application surface.

2. The applicator according to claim 1, wherein said two partial bodies being connected with one another, the two partial bodies further comprise means for disconnection of one partial body from another.

3. The applicator according to claim 1, further comprising a spring for holding said two partial bodies in the closed position.

4. The applicator according to claim 1, wherein said two partial bodies are rotatably connected to one another at a pivot means.

5. The applicator according to claim 4, wherein said two partial bodies rotate about the pivot means, the pivot means comprising a swivel axis which is perpendicular to the longitudinal axis of said two partial bodies.

6. The applicator according to claim 5, the pivot means further comprising a switch device to permit rotating about the swivel axis, wherein said swivel device comprises an axle passing through said two partial bodies and two guide plates for connection to the axle that are slideably seated in annular grooves of the two partial bodies.

7. The applicator according to claim 4, wherein said two partial bodies swivel about an axis of rotation which is arranged parallel to the longitudinal axis of said two partial bodies.

8. The applicator according to claim 7, wherein each of said two partial bodies further comprises a projection, said projections being swivelly connected with one another by a hinge forming said axis of rotation.

9. The applicator according to claim 4, further comprising a stop for preventing any further opening of said two partial bodies once said partial bodies have moved from the closed position to the open position through a predetermined angle with respect to one another.

10. The applicator according to claim 4, wherein said two extended partial bodies each further comprise an exchangeable cover, the cover for covering each extended partial body comprising the transducer elements unless stopped by the pivot means.

11. The applicator according to claim 10, wherein said two covers open into a common covering, the common covering for covering the pivot means.

12. The applicator according to claim 1, wherein said guide channel is located at either end of the central portion of said extended partial bodies in their closed position.

13. The applicator according to claim 1, wherein said guide channel of the extended partial bodies in their closed position is of continuous elongated embodiment along the central longitudinal axis of said carrying body.

14. The applicator according to claim 1, wherein said two extended partial bodies each comprise actuating cables connected to the bodies at one end such that the partial bodies and cables are mirror images of one another.

15. The applicator according to claim 1, wherein neighboring ultrasonic transducer elements of said two partial bodies, in their closed position are adjacently opposite one another and are in a perpendicular plane to and continually placed along the longitudinal axis and furthermore, are electrically connected in parallel and simultaneously controlled by a control device.

16. The applicator according to claim 1, further comprising means for ensuring that ultrasonic beams emitted by said ultrasonic transducer elements of said partial bodies are focused obliquely to the longitudinal axis of said partial bodies.

17. The applicator according to claim 16, wherein said two groups of transducer elements are positioned obliquely to the longitudinal axis of said partial bodies to permit said oblique focusing.

18. The applicator according to claim 1, wherein said two guide grooves are each only slightly deeper than one-half the diameter of said biopsy needle.

19. The applicator according to claim 1, wherein said two partial bodies are attached to one another by means of a resilient clamp.

20. An ultrasonic applicator for biopsy with a guide channel for receiving a biopsy device, said ultrasonic applicator comprising two partial applicators, each comprising ultrasonic transducer means, the two partial applicators being that rotatably connected with one another and operated parallel with one another, and which in a closed position form said guide channel with one another.

* * * * *

UNITED STATES PATENT AND TRADEMARK OFFICE
CERTIFICATE OF CORRECTION

PATENT NO. : 4,542,747

DATED : September 24, 1985

INVENTOR(S) : Zurinski et al.

It is certified that error appears in the above-identified patent and that said Letters Patent is hereby corrected as shown below:

Column 1, line 32, delete "split-image" and substitute --cross-sectional image producing--.
Column 1, line 35, delete "split-image" and substitute --cross-sectional image producing--.
Column 5, line 18, delete "split-image" and substitute --cross-sectional image producing--.
Column 6, line 1, delete "of" and substitute --on--.
Column 6, line 40, delete "in" ,second occurrence, to read -- is --.
Column 8, line 52, delete "FIG. 1" and substitute --FIG. 11--.
Column 8, line 65, after "it", insert --is--.
Column 10, line 31, delete "112" and substitute --122--.
Column 12, line 54, delete "that".

Signed and Sealed this

Eighteenth Day of March 1986

[SEAL]

Attest:

DONALD J. QUIGG

Attesting Officer

Commissioner of Patents and Trademarks